(12) United States Patent
Zoll et al.

(10) Patent No.: US 9,655,707 B2
(45) Date of Patent: May 23, 2017

(54) METHODS, COMPOSITIONS, DEVICES AND KITS FOR ATTACHING SURGICAL SLINGS TO TISSUE

(71) Applicant: Boston Scientific Scimed, Inc., Maple Grove, MN (US)

(72) Inventors: Jonathan Zoll, Brookline, MA (US); Peter J. Pereira, Mendon, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 17 days.

(21) Appl. No.: 14/614,669

(22) Filed: Feb. 5, 2015

(65) Prior Publication Data
US 2015/0216646 A1    Aug. 6, 2015

Related U.S. Application Data

(60) Provisional application No. 61/936,640, filed on Feb. 6, 2014.

(51) Int. Cl.
*A61F 2/00* (2006.01)
*A61B 18/22* (2006.01)
*A61N 5/06* (2006.01)
*A61B 18/00* (2006.01)

(52) U.S. Cl.
CPC ............ *A61F 2/0045* (2013.01); *A61B 18/22* (2013.01); *A61N 5/062* (2013.01); *A61B 2018/00619* (2013.01); *A61F 2002/0072* (2013.01)

(58) Field of Classification Search
CPC ... A61F 2/0063; A61F 2002/0068–2002/0072; A61F 2310/00389–2310/00976; A61F 2/848; A61F 2/0045; A61L 31/00–31/14; A61B 2018/00619
See application file for complete search history.

(56) References Cited

U.S. PATENT DOCUMENTS

| | | | |
|---|---|---|---|
| 5,292,362 A | 3/1994 | Bass et al. | |
| 5,552,452 A | 9/1996 | Khadem et al. | |
| 5,922,026 A * | 7/1999 | Chin ................. | A61B 17/0057 606/151 |
| 6,372,228 B1 * | 4/2002 | Gregory ............... | A61F 2/0063 424/400 |
| 6,391,049 B1 | 5/2002 | McNally et al. | |
| 6,875,427 B1 | 4/2005 | Devore et al. | |
| 2003/0114866 A1 | 6/2003 | Ulmsten et al. | |
| 2003/0191480 A1 | 10/2003 | Ulmsten et al. | |

(Continued)

FOREIGN PATENT DOCUMENTS

| | | |
|---|---|---|
| WO | 2006048885 A1 | 5/2006 |
| WO | 2015120117 A2 | 8/2015 |

OTHER PUBLICATIONS

Response to Non Final Office Action for U.S. Appl. No. 14/564,370, filed Jun. 21, 2016, 7 pages.
(Continued)

*Primary Examiner* — Catherine B Kuhlman
(74) *Attorney, Agent, or Firm* — Brake Hughes Bellermann LLP

(57) ABSTRACT

The present disclosure is directed to methods, compositions, devices and kits which pertain to the attachment of surgical slings to tissue by application of an energy source to the slings and tissue in the presence of a bonding material.

7 Claims, 6 Drawing Sheets

(56) References Cited

U.S. PATENT DOCUMENTS

| | | | |
|---|---|---|---|
| 2004/0215231 A1 | 10/2004 | Fortune et al. | |
| 2005/0010239 A1 | 1/2005 | Chefitz | |
| 2006/0058578 A1* | 3/2006 | Browning | A61B 17/0401 600/37 |
| 2006/0195010 A1* | 8/2006 | Arnal | A61B 17/06066 600/30 |
| 2008/0004686 A1* | 1/2008 | Hunt | A61F 2/2418 623/1.11 |
| 2008/0132753 A1* | 6/2008 | Goddard | A61B 17/06109 600/37 |
| 2008/0177132 A1* | 7/2008 | Alinsod | A61F 2/0045 600/37 |
| 2009/0171377 A1 | 7/2009 | Intoccia et al. | |
| 2009/0304773 A1 | 12/2009 | Milbocker et al. | |
| 2010/0104608 A1 | 4/2010 | Abuzaina et al. | |
| 2011/0054249 A1* | 3/2011 | Narthasilpa | A61B 17/00491 600/37 |
| 2012/0029274 A1* | 2/2012 | Goddard | A61B 17/06166 600/37 |
| 2012/0253339 A1* | 10/2012 | Rick | A61F 2/0063 606/33 |
| 2012/0271290 A1* | 10/2012 | Sargeant | A61B 18/18 606/14 |
| 2013/0190245 A1 | 7/2013 | Soltz et al. | |
| 2013/0225918 A1 | 8/2013 | Harrah et al. | |
| 2014/0309626 A1* | 10/2014 | Sargeant | A61F 2/0063 606/14 |
| 2015/0157439 A1* | 6/2015 | Zoll | A61L 31/10 600/37 |
| 2015/0216646 A1 | 8/2015 | Zoll et al. | |
| 2015/0314035 A1* | 11/2015 | Rolfes Meyering | A61K 9/0024 600/37 |
| 2015/0374516 A1 | 12/2015 | Pereira et al. | |

OTHER PUBLICATIONS

Non Final Office Action for U.S. Appl. No. 14/564,370, mailed Mar. 25, 2016, 15 Pages.

International Search Report and Written Opinion for PCT Application No. PCT/US2015/014566, mailed Sep. 22, 2015, 15 pages.

International Preliminary Report and Written Opinion for PCT Application PCT/US2016/014566, mailed on Aug. 18, 2016, 11 pages.

Non Final Office Action for U.S. Appl. No. 14/564,370, mailed on Aug. 29, 2016, 20 pages.

* cited by examiner

METHODS, COMPOSITIONS, DEVICES AND KITS FOR ATTACHING SURGICAL SLINGS TO TISSUE

STATEMENT OF RELATED APPLICATION

This application claims the benefit of U.S. Provisional Application Ser. No. 61/936,640, filed Feb. 6, 2014, the entire disclosure of which is hereby incorporated by reference in its entirety.

FIELD OF THE INVENTION

The present invention relates to methods, compositions, devices and kits for the attachment of surgical slings to tissue.

BACKGROUND

Urinary incontinence affects millions of men and women of all ages in the United States. Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results. A common treatment of SUI is via the use of a surgical sling which is permanently placed under a patient's bladder neck or mid-urethra to provide a urethral platform. Placement of the sling limits the endopelvic fascia drop, while providing compression to the urethral sphincter to improve coaptation.

SUMMARY OF THE INVENTION

The present invention relates to methods, compositions, devices and kits for the attachment of surgical slings to tissue.

According to one aspect, the present invention is directed to surgical slings having two ends and comprising a sling material and a bonding material associated with at least the two ends of the sling, wherein each end of the sling is configured to be inserted into or through an incision or puncture in patient tissue and is configured to bond to the patient tissue when exposed to an energy source after insertion.

According to another aspect, the present invention is directed to methods of surgically attaching such surgical slings to patient tissue, comprising inserting an end of the sling into an incision or puncture in patient tissue and using energy from an energy source to apply energy to the bonding material, such that the bonding material is activated and the end of the sling is attached to the tissue.

According to another aspect, the present invention is directed to surgical instruments that comprise a handle, an elongated member comprising a distal tip that is configured to receive and place a surgical sling in a subject, and an energy source proximate the distal tip.

According to yet another aspect, the present invention is directed to kits that comprise a combination of any two or more of the following items: (a) a surgical sling, either with or without an associated bonding material, having ends that are configured to be held and placed by a surgical delivery device, (b) a bonding material in solid form or in fluid form, (c) a surgical delivery device, either with or without an associated energy source, that is configured to receive and place a surgical sling in a subject, and (d) an energy source.

These and other aspects, as well as various embodiments and advantages of the present invention will become immediately apparent to those of ordinary skill in the art upon review of the Detailed Description and claims to follow.

DETAILED DESCRIPTION

Figure 1:
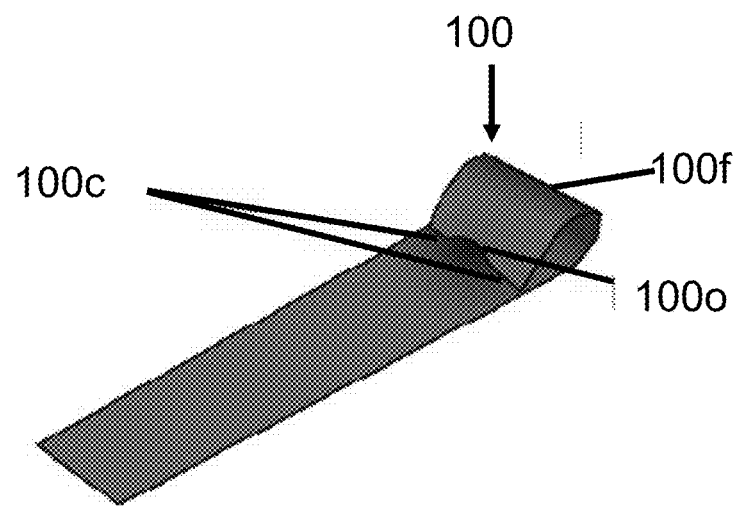
FIG. 1 is a schematic illustration of an end of a surgical sling, in accordance with an embodiment of the present invention.

A more complete understanding of the present invention is available by reference to the following detailed description of numerous aspects and embodiments of the invention. The detailed description which follows is intended to illustrate but not limit the invention.

The present disclosure pertains to methods, compositions, devices and kits that are useful in medical procedures, including urinary continence repair, among others. In various embodiments, slings are used to support the urethra to aid in urine retention. Slings are commonly held in place by friction, tangs on a mesh, carriers and/or anchors. Fixation by friction or tangs on the mesh typically requires the sling to traverse a considerable length of tissue to provide the necessary holding force, which may result in unnecessary trauma for the tissue. Similarly, carriers and anchors (e.g., barbs, etc.) may create discomfort or prolong healing (e.g., where the carrier or anchor is affixed to the obturator muscle). In the present disclosure, tissue bonding technology is used as a technique for attaching surgical slings to tissue, which may eliminate the need to traverse considerable lengths of tissue and/or the need for carriers and/or anchors. In other embodiments, tissue bonding technology may supplement the use of tangs, carriers and/or anchors.

In some aspects of the present disclosure, methods of attaching slings in urogynecological procedures are provided wherein tissue soldering technology is used to bond a sling to tissue. This is achieved by placing a sling material and a bonding material in intimate association with patient tissue and then applying energy from an energy source to activate the bonding material and bond the sling to the tissue. For example, in some embodiments, a sling comprising a sling material and an associated bonding material is placed into or though incisions or punctures in patient tissue (e.g., in the obturator muscle, abdominal wall, etc.). Energy is then applied to the tissue and sling such that the solder bonds the sling material to the tissue.

Thus, in various aspects of the present disclosure, surgical slings are provided which comprise a sling material and a bonding material associated with the sling material and which are configured to bond to patient tissue when exposed to an energy source while the surgical sling is in contact with the tissue. For example, a sling material may be associated with a bonding material by providing a coating of a bonding material on all or a portion of a sling material or by incorporating a bonding material into all or a portion of a sling material, among other strategies. In certain embodiments, the sling may be provided with features such as pockets which allow the sling to be delivered and fixated by pressing the sling into incisions or punctures in tissue, or with features such as sutures, which allow the sling to be pushed and/or pulled into and/or through a puncture or incision in tissue.

Different energy sources may be used for sling attachment, depending on the mechanism for tissue bonding that is employed. The energy source may be, for example, a source of heat or light, such as a laser, a light-emitting diode (LED). Infrared and near-infrared laser sources include carbon dioxide ($CO_2$), thulium-holmium-chromium, holmium, thulium, and neodymium rare-earth-doped-garnets (THC:YAG, Ho:YAG, Tm:YAG, and Nd:YAG, respectively), and gallium aluminum arsenide diode (GaAlAs) lasers, among others. Visible sources include potassium-titanyl phosphate (KTP) frequency-doubled Nd:YAG, and argon lasers, among others. Other energy sources include radiofrequency sources (e.g., a microwave source), radiation sources (e.g., x-ray radiation, gamma radiation, etc.), and a locally produced plasma, among others. Argon plasmas are currently employed in various medical applications, including argon beam coagulators, which ionize argon gas to form an argon plasma and then use the plasma to deliver thermal energy to nearby tissue. In the present disclosure, an argon beam may be used as a source of heat for tissue bonding. Other energy sources include radiation (e.g., x-ray radiation, gamma radiation, etc.).

In certain embodiments, the energy source is a handheld energy source.

In certain embodiments, the energy source is provided in a stand-alone unit. In other embodiments, the energy source is combined with another device. For example, the energy source may be combined with a sling delivery device, such as that described below, thereby creating a single unit that can hold, place and seal a sling to tissue.

In some embodiments, the energy source is connected to a control unit, which controls the energy emitting from the energy source. Preferably, the amount of energy is sufficient to activate the bonding material without significantly damaging the underlying tissue. In some embodiments, the control unit is designed to accept user input (e.g., via physical buttons, touchscreen, etc.), thereby allowing treatment parameters to be set by a health care provider.

In some embodiments, the energy source is controlled without the use of a sensor (e.g., based on the experience of the surgeon or based on a suitable energy output algorithm). In other embodiments, a sensor is used in conjunction with the energy source to provide feedback regarding the amount of energy being directed to the bonding site, and this feedback can be used to adjust the energy source output. For example, in certain embodiments, the sensor is a temperature sensor which detects the amount of heat at the bonding site. In these embodiments, suitable software can be employed to adjust the output of the energy source based on input from the temperature sensor. The sensor may be provided, for example, in the same device as the energy source or in a device that is different from the device containing the energy source. The sensor may be provided, for example, in a medical device that is used for sling delivery (either with or without the energy source).

A variety of bonding materials can be used in conjunction with the present disclosure.

In this regard, laser tissue soldering processes are known in the surgical art whereby tissue is bonded by applying a solder (commonly, a biological polymer) to the tissue after which a laser is used to activate the solder and form a bond. Without wishing to be bound by theory, it has been reported that the mechanism of laser tissue soldering appears to include a heating-induced protein denaturation-renaturation process. See, e.g., B. Forer et al., *Laryngoscope* 116: June 2006, 1002-1006.

Solder materials are used in the present disclosure as bonding materials to bond sling materials to tissue, for example, by the application of heat to a solder material while it is in contact with a sling material and tissue, such that the sling material is bonded to the tissue. As indicated above, beneficial energy sources for the application of heat include light sources (e.g., lasers, etc.), radiofrequency sources (e.g., microwave sources, etc.) and plasma sources (e.g., argon beams, etc.), among others.

Particularly beneficial solder materials have a relatively low activation temperature and are bio-absorbable. Over time (typically between about 4 and 60 days, depending on the solder that is used), the solder may be bioabsorbed (with the bioabsorption rate being adjustable within this range, or to sooner than or after this range, by adjusting the chemistry of the solder), leaving only the sling material and tissue growth behind.

Specific solder materials for use in conjunction with the present disclosure include solders of biological origin and synthetic solders. Examples of solders of biological origin include those based on biological polymers, for example, polypeptides including nano-peptides and proteins such as albumin, collagen, elastin, fibrinogen, and fibrin, protein derivatives, as well as polysaccharides including chitosan, among others. Examples of solders of synthetic origin include polylactide, polyglycolide, poly(glycerol sebacate acrylate), and poly(lactide-co-glycolide). In some embodiments, two, three, four or more solder materials such as those described above are employed. Specific examples include a combination of albumin and collagen, a combination of albumin and chitosan, a combination of collagen and chitosan, and a combination of albumin, collagen, and chitosan, among many other possible combinations.

In some embodiments, at least one energy absorber is used within the solder material to enhance heating efficiency and/or heat distribution within the solder material. Energy absorbers include chromophores, for example, light-specific dyes such as indocyanine green (ICG), fluorescein, basic fuchsin, and fen, nano-gold (e.g., gold nanorods, gold nanoshells, gold nanocages, etc.), SPIONs (superparamagnetic iron oxide nanoparticles), and silica nanoparticles, among other materials. Specific examples include ICG-doped albumin, fluorescein-dye-doped albumin, and nano-gold-doped albumin, among many others.

Photochemical tissue bonding processes are known the surgical art. These processes take advantage of the photochemical reactions that occur at intimately associated tissue surfaces, which are stained with a photosensitizing dye (e.g., dyed tissue surfaces which are placed in contact with one another). Without wishing to be bound by theory, it is believed that the dye absorbs photons of visible radiation and promotes the formation of covalent bonds between molecules on the approximated tissue surfaces. For example, reactive species that are produced upon light activation of the dye can react with potential electron donors and acceptors such as amino acids in proteins (e.g., tryptophan, tyrosine, cysteine, and so forth). In this regard, photochemical methods have been reported to form crosslinks in collagen type I molecules. See, Barbara P. Chan et al., *Journal of Surgical Research* 108, 77-84 (2002).

In certain aspects of the present disclosure, photosensitizing dyes are used to bond sling materials to tissue surfaces, for example, by the application of light of a suitable wavelength to a photosensitizing dye and a solder material (e.g., a biological solder material, including those set forth above, among others) in intimate association with a sling material and a tissue surface (e.g., a photosensitizing dye admixed with a solder material or coated on a surface of a solder material that is in contact with and disposed between sling material and tissue), such that the sling material is bonded to the tissue. A light-emitting energy source such as a low-power laser or light-emitting diode (LED) may be used for this purpose, among others.

Specific examples of photosensitizing dyes include xanthene dyes such as rose bengal, methylene blue and fluorescein, riboflavin dye (e.g., riboflavin-5-phosphate), lumichrome dye, lumiflavin dye, Reactive Black 5, thiazine dye, erythrosine, N-hydroxypyridine-2-(1H)-thione (N-HTP), protoporphyrin I through protoporphyrin IX, coproporphyrins, uroporphyrins, mesoporphyrins, hematoporphyrins and sapphyrins, chlorophylis, e.g., bacteriochlorophyll A, Photofrin®, synthetic diporphyrins and dichlorins, phthalocyanines with or without metal substituents, chloroaluminum phthalocyanine with or without varying substituents, O-substituted tetraphenyl porphyrins, 3,1-meso tetrakis (o-propionamido phenyl) porphyrin, verdins, purpurins, tin and zinc derivatives of octaethylpurpurin, etiopurpurin, hydroporphyrins, bacteriochlorins of the tetra(hydroxyphenyl) porphyrin series (e.g., protoporphyrin I through protoporphyrin IX, coproporphyrins, uroporphyrins, mesoporphyrins, hematoporphyrins and sapphyrins), chlorins, chlorin e6, mono-1-aspartyl derivative of chlorin e6, di-1-aspartyl derivative of chlorin e6, tin(IV) chlorin e6, meta-tetrahydroxphenylchlorin, benzoporphyrin derivatives, benzoporphyrin monoacid derivatives, tetracyanoethylene adducts of benzoporphyrin, dimethyl acetylenedicarboxylate adducts of benzoporphyrin, Diels-Adler adducts, monoacid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, chlorophylis, bacteriochlorophyll A, anthracenediones, anthrapyrazoles, amino-anthraquinone, phenoxazine dyes, phenothiazine derivatives, chalcogenapyrylium dyes, cationic selena and tellurapyrylium derivatives, ring-substituted cationic PC, pheophorbide derivative, naturally occurring porphyrins, hematoporphyrin, ALA-induced protoporphyrin IX, endogenous metabolic precursors, 5-aminolevulinic acid, benzonaphthoporphyrazines, cationic imminium salts, tetracyclines, lutetium texaphyrin, texaphyrin, tin-etio-purpurin, porphycenes, benzophenothiazinium, eosin, erythrosin, cyanines, merocyanine 540, selenium substituted cyanines, flavins, riboflavin, proflavin, quinones, anthraquinones, benzoquinones, naphthaldiimides, naphthalimides, victoria blue, toluidine blue, dianthroquinones (e.g., hypericin), fullerenes, rhodamines and photosensitive derivatives thereof.

An advantage of using light rather than heat is that there is less risk of causing damage to the tissue (cell death) from heat. Another advantage of using light, rather than heat, to achieve sling-to-tissue bonding is that complications due to uneven heat distribution can be reduced or eliminated.

In addition, the use of wavelength-specific absorbers such as chromophores enables differential absorption between the chromophore-containing regions and surrounding tissue. One advantage is a selective absorption of radiation by the target, without the need for a precise focusing. Moreover, lower power levels may be used because of the increased absorption of chromophore-containing regions, leading to reduced tissue damage.

Sling materials for use in accordance with the present disclosure include various synthetic and natural polymers. Beneficial polymers for forming slings may be selected from the following, among others: (a) polyolefin homopolymers and copolymers, including homopolymers and copolymers of C2-C8 alkenes, for example, polyethylene and polypropylene among others, (b) fluoropolymers, including homopolymers and copolymers of C2-C8 alkenes in which one or more hydrogen atoms are substituted with fluorine, for example, polytetrafluoroethylene (PTFE), polyvinylidene fluoride (PVDF), poly(vinylidene fluoride-co-hexafluoropropene) (PVDF-HFP) among others, (c) polyamides such as nylons, among others, (d) polyesters, including, for example, polyethylene terephthalate, among others, (e) polyurethanes such as polyisobutylene based polyurethanes (PIB-PU) that comprise one or more polyisobutylene segments, among others, (f) polyoxyalkylenes including homopolymers of trioxane (e.g., polytrioxane, also known as polyoxymethylene or acetal) and copolymers of trioxane (e.g., copolymers of trioxane and dioxane) and (g) styrenic copolymers such as alkene-styrene copolymers, including block copolymers comprising one or more polystyrene blocks and one or more polyalkene blocks, for instance, poly(styrene-b-isobutylene-b-styrene) (SIBS), poly(styrene-b-ethylene/butylene-b-styrene) (SEBS).

Sling materials may be in the form of a mesh formed from one or more fibers. Consequently, surgical slings in accordance with the present disclosure may be formed using a variety of fiber-based construction techniques and include, for example, woven slings and non-woven slings (e.g., knitted, braided, coiled, randomly wrapped, spunbound, etc.).

The overall fiber width (e.g., the diameter of circular fibers) in the slings of the present disclosure may vary widely. In certain embodiments, the surgical slings of the present disclosure may have fiber widths ranging from 50 µm to 200 µm, among other values.

In certain embodiments, fibers may be provided with surface features, for example, to increase the surface area of the fibers and thus the contact area between the fibers and a solder material coating.

Surgical claims in accordance with the present disclosure may also have a wide range of pore sizes. In various embodiments, the surgical slings of the present disclosure may have area pore sizes that are ≥0.25 mm$^2$ with a minimum axis of 0.5 mm. In various embodiments, the pore size can be varied, for example, to modify tissue in-growth properties. Slings include Type I slings, which are macroporous prostheses (i.e., with pores >75 µm), Type II slings, which are microporous prostheses (i.e., pores <10µ) and Type III slings, which are macroporous prostheses with multifilamentous or microporous components.

In certain embodiments, slings may be provided with one or more features that allow one or both ends of the sling to be pressed into an incision or puncture in tissue. For example, one or both ends of the slings may each be provided with one or more pockets for engaging a sling delivery device.

Bonding material may be associated with sling material in various ways. For example, sling material may be admixed or impregnated with bonding material, sling material may be coated with bonding material, a sheet of bonding material may be laminated to sling material, and so forth. Sling material may be impregnated and/or coated with bonding material either before a sling is formed (e.g., when the sling material is in fiber form) or after a sling is formed.

The bonding material may be present, for example, throughout the entire sling or on only a portion of the sling, for instance, associated with the ends of the sling. This allows portions of the sling to be largely free of bonding material, which reduces bonding material consumption.

Sling material may be impregnated and/or coated with bonding material using various techniques which may be selected, for example, from dipping techniques, spraying techniques, spin coating techniques, web coating techniques, electrostatic techniques, techniques in which bonding material is selectively applied to certain regions of the sling but not others, for example, through the use of a suitable application device such as a sprayer, brush, roller, pen, or printer (e.g., screen printing device, ink jet printer, etc.). A partial or complete bonding material coating may also be formed by coextruding the sling material with bonding material.

Surgical slings in accordance with the present disclosure include mini-slings, retropubic slings and transobturator slings, among others. Depending on the procedure, slings in accordance with the present disclosure may be implanted by one or more of the following routes, among others: transvaginally (e.g., by vaginal incision), laparoscopically, and via open abdominal surgery (laparotomy). Surgical slings may be surgically implanted in a variety of subjects, typically vertebrate subjects, more typically mammalian subjects, including human subjects, pets and livestock.

Turning now to the drawings, there is schematically illustrated in FIG. 1, one end of a sling 100, which may comprise, for example, a woven or non-woven fiber sling material which is associated with a bonding material (e.g., a solder material, which may or may not be associated with a photosensitizing dye, etc.). In some embodiments, the sling 100 may include a coating of bonding material that covers all or only a portion (e.g., the ends) of the sling material, among other possibilities. The sling 100 is folded horizontally to form a fold 100f and the sling is connected to itself near each edge 100c leaving and opening 100o in the center for a delivery device to fit into, such that the sling can be pushed into tissue.

Figure 2:
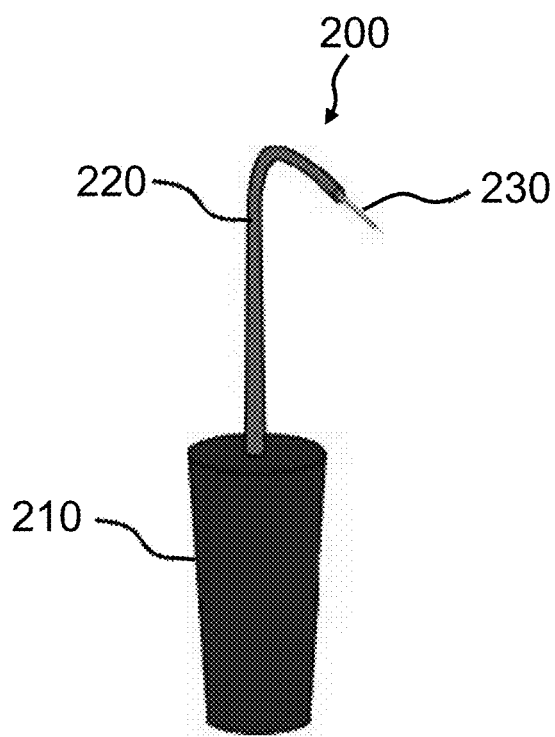
FIG. 2 is a schematic illustration of a sling delivery device, in accordance with an embodiment of the present invention.

FIG. 2 is a schematic illustration of a device 200 for implanting slings in accordance with an embodiment of the disclosure. The device 200 shown is a handheld device includes a handle portion 210 and an elongated portion 220. Extending from the elongated portion 220 is a sharp tip 230 which, in some embodiments, may be used to penetrate tissue to form small punctures or tunnels in the tissue. The tip 230 may also be supplied with an energy source, for instance, an internal optical fiber or light emitting diode, in some embodiments. The elongated portion 220 has a curved or angled shape. The elongated portion 220 may, for example, be inserted into a pocket located at the end of a sling like that of FIG. 1, and it may be used to deliver the sling to a desired tissue location and initially affix the sling in place by pressing the sling into a puncture or incision that is formed in the tissue. Subsequently, energy is applied from an energy source to activate the bonding material and bond the sling to the tissue.

In one particular embodiment, the sling is implanted by first incising the anterior vaginal wall at the level of the mid-urethra and then dissecting bilaterally to the interior portion of the inferior pubic ramus, thereby creating a pathway for sling placement. A sling like that of FIG. 1 may be placed on a delivery device like that of FIG. 2 by inserting the delivery device tip into the pocket at one end of the sling. The delivery device with attached sling is then advanced along the dissection pathway and the end of the device pressed into obturator internus muscle tissue (e.g., in an incision or puncture previously made in the obturator internus muscle, etc.), thereby depositing the end of the sling into the tissue. The surgeon can then apply energy (e.g., laser or light) to bond the sling to the tissue. The delivery device may, for example, contain an energy source at its tip, which is activated after depositing the sling in the tissue but prior to retracting the delivery device. As the device is retracted, the solder coated sling and tissue are exposed to energy, thereby bonding the sling to the tissue. In other embodiments, a separate device with energy source is used to apply energy to the site. This procedure is then repeated contralaterally with the other end of the sling (not shown in FIG. 1).

Figure 3:
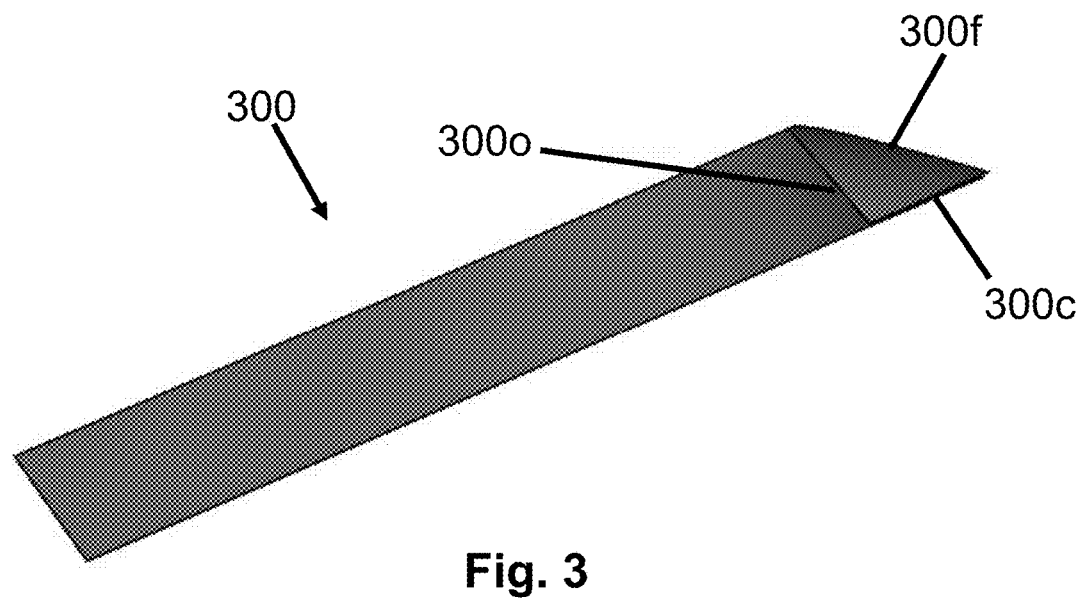
FIG. 3 is a schematic illustration of an end of a surgical sling, in accordance with another embodiment of the present invention.
Figure 4:
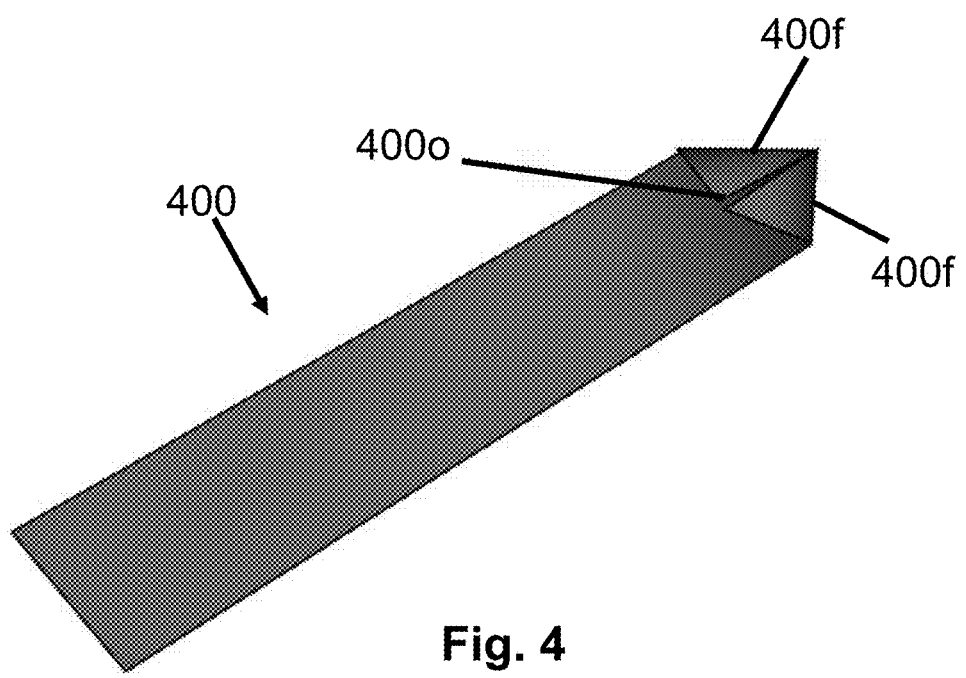
FIG. 4 is a schematic illustration of an end of a surgical sling, in accordance with yet another embodiment of the present invention.

FIGS. 3 and 4 are schematic illustrations of the ends of two slings 300, 400, which may comprise, for example, a woven or non-woven fiber sling material which is associated with a bonding material (e.g., a solder material, which may or may not be associated with a photosensitizing dye, etc.). In some embodiments, the slings 300,400 may include a coating of bonding material that covers all or only a portion (e.g., the ends) of the sling material, among other possibilities. In FIG. 3, the sling 300 is folded diagonally to form a fold 300f and the sling is connected to itself along the edge 300c forming an opening 300o in the center of the sling 300 for a delivery device to fit into. In FIG. 4, on the other hand, the sling 400 is folded diagonally from two sides to form two folds 400f. The sling 400 is connected to itself forming an opening 400o for the delivery device to fit into.

Figure 5:
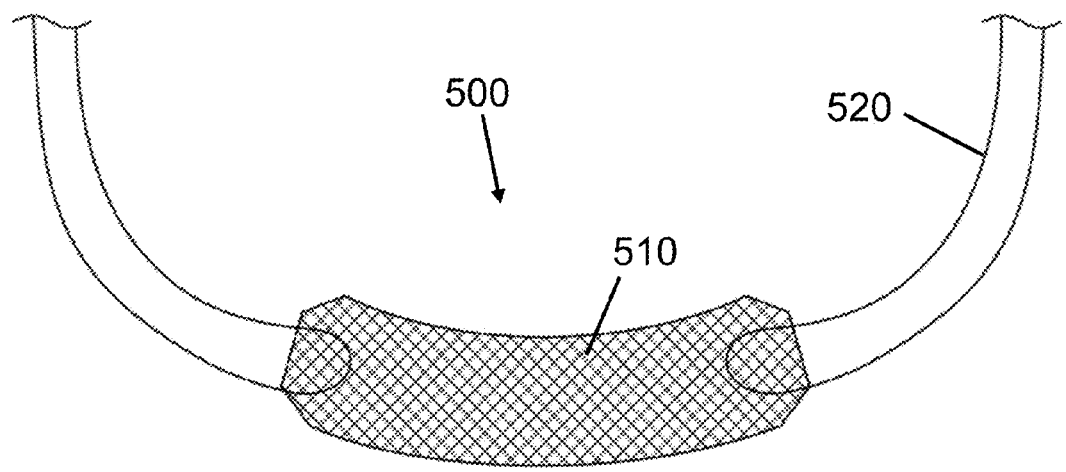
FIGS. 5 and 6 are schematic illustrations of surgical slings, in accordance with further embodiments of the present invention.
Figure 6:
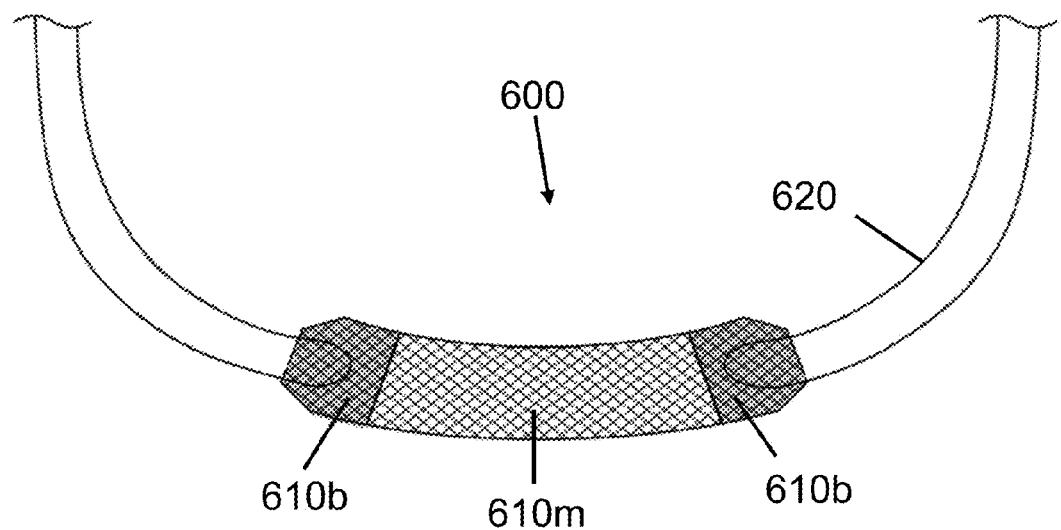

In other embodiments, slings are provided with features that allow the slings to be pulled through incisions or punctures (e.g., incisions or punctures that traverse a tissue wall). For example, FIG. 5 is a schematic illustration of a device 500 which includes a sling portion 510 in the form of a fiber mesh material that is completely covered in bonding material and sutures 520 attached to the ends of the sling portion. FIG. 6 is also a schematic illustration of a device 600 which includes a sling portion 610 in the form of a fiber mesh material 610m that is coated on each end with bonding material 610b and sutures 620 attached to the ends of the sling portion.

Such slings may be delivered, for example, either retropubicly or transobturatorly with the use of a low profile needle. The suture protrudes through the skin once passed through the abdominal tissue. Once in position, the surgeon applies energy to one end of the sling to bond the sling to tissue on one side. The energy may be applied internally to the subject and/or externally. In some embodiments, the device containing the energy source is has a narrow tip which can be inserted into the incision or puncture through which the sling passes, thereby allowing energy to be applied in the interior of the puncture or incision. Once the sling is attached, the suture on that side can be removed. The surgeon can then apply the required tension on the other side by pulling the suture. Once the correct tension is applied, the surgeon can clamp the suture to hold the tension. The surgeon can then apply energy to that end of the sling to attach the mesh to tissue. The second suture can then be removed.

Figure 7:
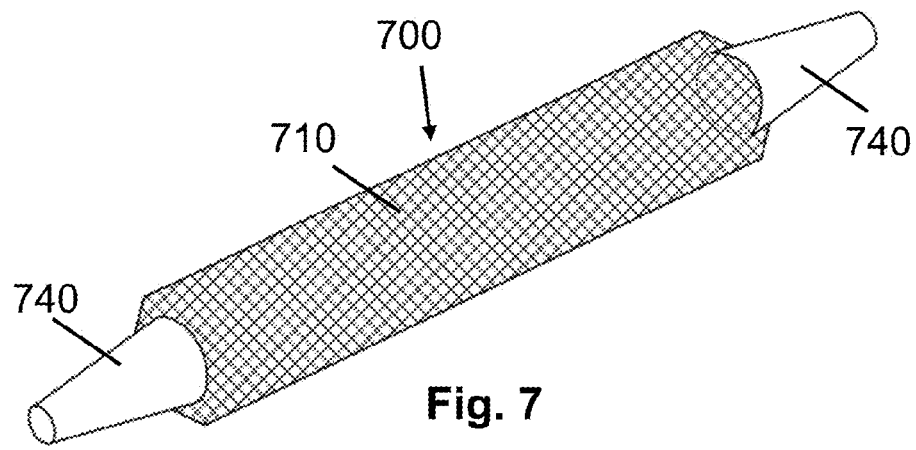
FIG. 7 is a schematic illustration of a surgical sling, in accordance with an embodiment of the present invention.

In accordance with another embodiment, and with reference to FIG. 7, a sling 700 (e.g., a minisling, etc.) may be provided, which includes a fiber mesh material 710. The mesh material may be uncoated with bonding material, completely coated with bonding material, or partially coated (e.g., on each end) with bonding material. The device is also provided with carriers 740 that have a partial conical shape (e.g., a funnel shape). The carriers 740 may be formed of a bonding material or may be formed of a biostable or bioabsorbable material that is partially (e.g., on the outside surface only) or completely coated with a bonding material. If made from a biostable implant material (e.g., polypropylene, etc.), the carrier can be provided with holes for tissue ingrowth. The carriers 740 may or may not further include additional fixation features such as 3-dimensional protrusions (e.g., teeth, spikes, tines, prongs, cones, etc.) that extend outward beyond the overall funnel shape.

The carriers 740 may be configured to lock onto a suitable delivery device. One example of a delivery device is a device 1300 like that shown in FIG. 13, which includes a handle 1355, elongate member 1360, and deployment mechanism 1370 (e.g., a pusher) similar to the Solyx™ SIS System from Boston Scientific, Natick, Mass., USA. However, in the embodiment shown, the delivery device 1300 includes an elongate member 1360 having an energy emitting tip 1360t. In embodiments where the sling is provided with a suitable carrier (see e.g., FIG. 7), the carrier may be locked in place on the tip of the delivery device. Activation of the deployment mechanism 1370 releases the carrier. In embodiments where there is no carrier (see, e.g., FIG. 12), activation of the deployment mechanism 1370 pushes the mesh off the tip of the delivery device 1300. In either case, activation of the deployment mechanism 1370 may also simultaneously energize the energy source, allowing energy to be applied to the site. The deployment mechanism 1370 may be locked to prevent inadvertent release of the carrier and energy.

Figure 8:
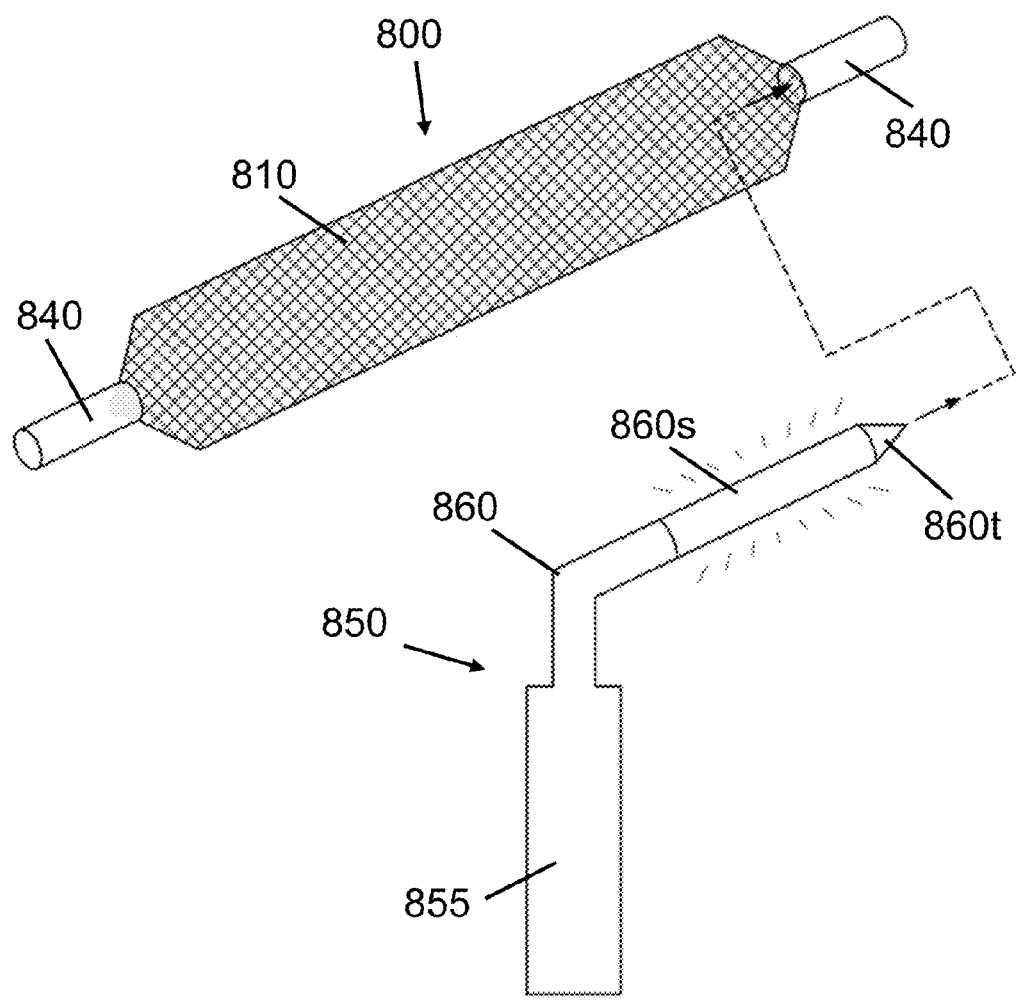
FIG. 8 is a schematic illustration of a surgical sling and a sling delivery device, in accordance with an embodiment of the present invention.

In accordance with another embodiment, and with reference to FIG. 8, a sling 800 (e.g., a minisling, etc.) may be provided which includes a fiber mesh material 810. The mesh material may be uncoated with bonding material, completely coated with bonding material, or partially coated (e.g., on each end) with bonding material. The device is also provided with carriers 840 that have a hollow cylindrical shape. The carriers may be formed of bonding material or may be formed of a biostable or bioabsorbable material that is partially (e.g., on the outside surface only) or completely coated with a bonding material. If made from a biostable implant material (e.g., polypropylene, etc.), the carrier can be provided with holes for tissue ingrowth. The carrier 840 may or may not feature additional fixation features such as 3-dimensional protrusions (e.g., teeth, spikes, tines, prongs, cones, etc.) that extend outward beyond the overall funnel shape. The carriers 840 may be configured to lock onto a suitable delivery device. In one embodiment, the cylindrical shaped carrier 840 may be delivered with a surgical tool 850 like that shown in FIG. 8, which has a handle 855 and an elongated portion 860 (e.g., curved or, in this case, angled) that includes pointed distal tip 860t and a section 860s proximal the distal tip that disperses energy radially.

Figure 9:
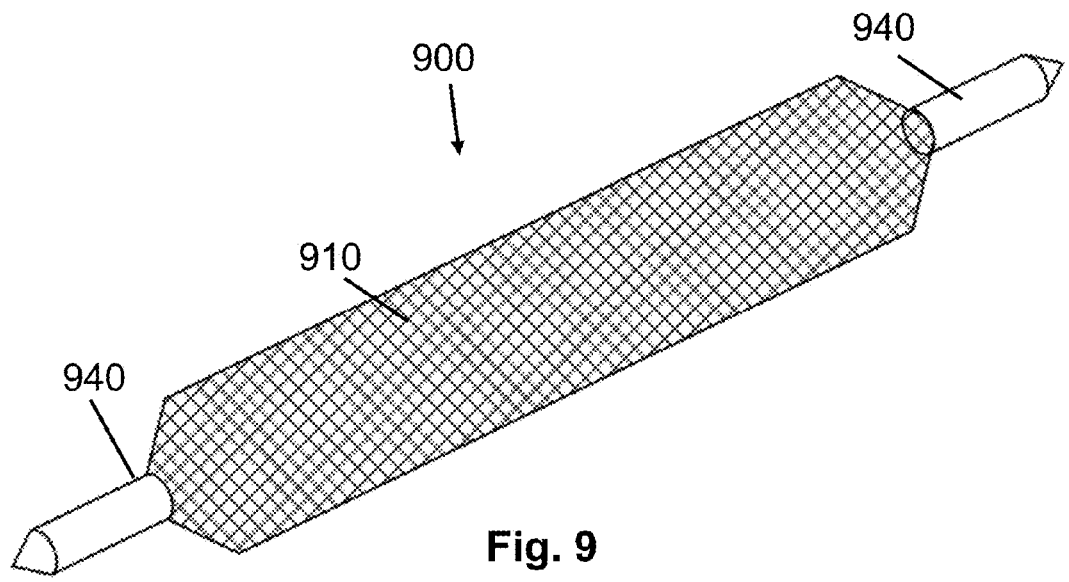
FIG. 9 is a schematic illustration of a surgical sling, in accordance with an embodiment of the present invention.
Figure 10:
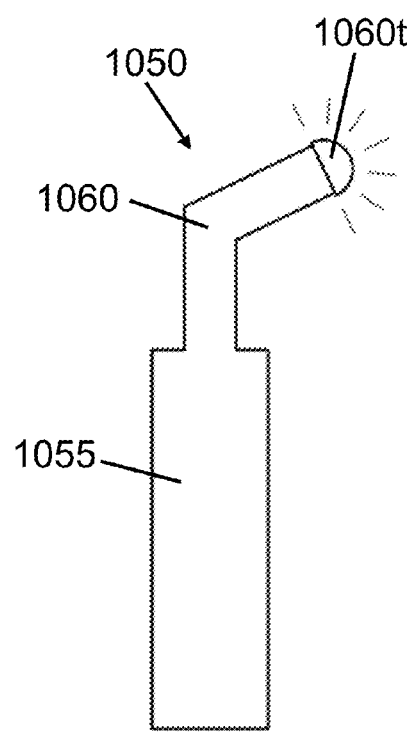
FIGS. 10 and 11 are schematic illustrations of sling delivery devices, in accordance with two embodiments of the present invention.
Figure 11:
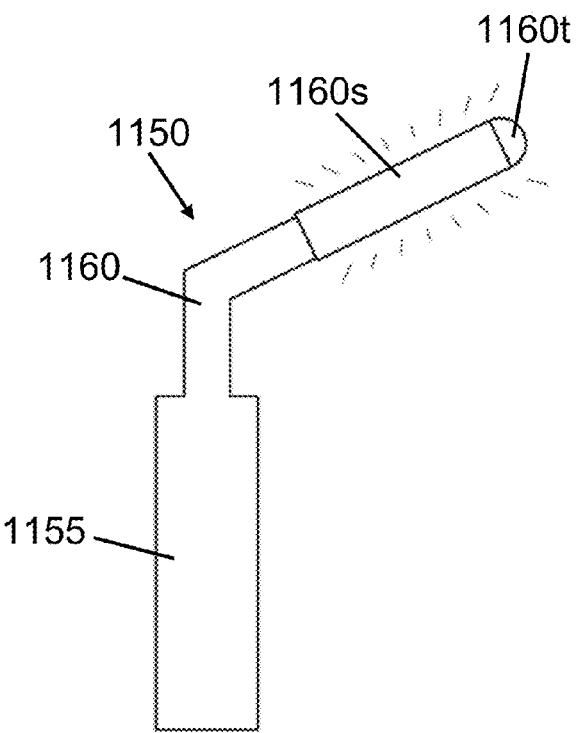

In accordance with yet another embodiment, and referring to FIG. 9, a sling 900 (e.g., a minisling, etc.) may be provided which includes a fiber mesh material 910. The mesh material may be uncoated with bonding material, completely coated with bonding material, or partially coated (e.g., on each end) with bonding material. The device is also provided with carriers 940 that have a hollow cylindrical shape and a pointed tip. Each carrier 940 may be formed of a bonding material or may be formed of a biostable or bioabsorbable material that is partially (e.g., only the ends) or completely coated with a bonding material. If made from a biostable implant material (e.g., polypropylene, etc.), the carrier 940 can be provided with holes for tissue ingrowth. The carrier 940 may or may not feature additional fixation features such as 3-dimensional protrusions that extend radially outward beyond the overall funnel shape (e.g., teeth, spikes, tines, prongs, etc.). The carriers 940 may be configured to lock onto a suitable delivery device that may or may not have a pointed tip. For example, the sling 900 may be delivered with a surgical tool 1050 like that shown in FIG. 10, which has a handle 1055 and a curved or angled elongated member 1060 having an energy emitting tip 1060t, or with a surgical tool 1150 like that shown in FIG. 11, which has a handle 1155 and a curved or angled elongated member 1160 having an tip 1160t and an energy emitting section 1060s that emits energy from the side of the elongated member 1060, among others.

Figure 12:
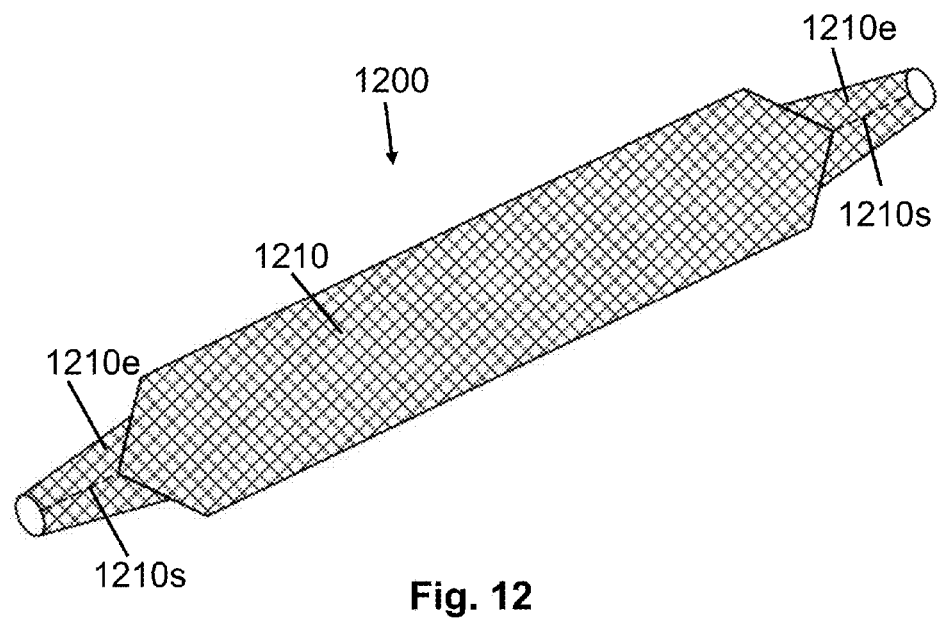
FIG. 12 is a schematic illustration of a surgical sling, in accordance with an embodiment of the present invention.
Figure 13:
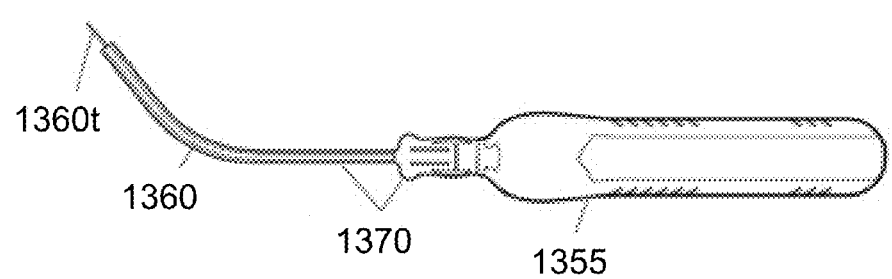
FIG. 13 is a schematic illustration of a sling delivery device, in accordance with an embodiment of the present invention.

In yet another embodiment, and referring to FIG. 12, a sling 1200 may be provided which comprises a fiber mesh material 1210. The ends 1210e of the fiber mesh material 1210 are knitted, braided, or wrapped and bonded together to form a channel. For example, the sling can be made from braided mesh in which a braided channel is formed, or the edges of the fiber mesh portion 1210 may be folded or wrapped and bonded together (e.g., sewn, glued, etc.) as shown in FIG. 12 to form a seam 1210s (as well as a channel). The entire sling 1200 may be coated with a bonding material or only the ends 1210e of the mesh may be coated with a bonding material. The sling 1200 may be delivered, for example, with a surgical tool like that shown in FIG. 8, which has a handle, a pointed tip, and a section that disperses energy radially, among others. In the preceding embodiments, the sling and the bonding material are applied to the tissue simultaneously (e.g., the sling material is coated, impregnated or otherwise associated with the bonding material).

In some embodiments, bonding material is applied to the site independently of the sling, in which case the sling either may be associated with bonding material at the time of application or free of bonding material at the time of application. In these embodiments, the bonding material may be applied to tissue followed by the sling, or the sling may be applied to tissue followed by the bonding material. The independently applied bonding material may be applied in solid form, fluid form or a combination thereof. In certain embodiments, the independently applied bonding material may be applied in the form of a fluid, for example, a liquid, paste or gel (e.g., an organic or aqueous liquid, paste or gel comprising a solider material and/or photosensitizing dye), which is injected into an incision or puncture in tissue. In certain embodiments, the independently applied bonding material may be applied in the form of an elongated solid (e.g., with a sharpened tip), which is inserted into an incision or puncture in tissue.

In certain embodiments, the slings of the present disclosure may comprise various additional agents other than those discussed above, including therapeutic agents and imaging agents, among other possible agents. Such agents may be, for example, incorporated into all or a portion of a sling material, or such agents may be applied in a coating (e.g., admixed with a bonding material or independent of a bonding material) over all or a portion of a sling material, among other strategies.

"Therapeutic agents," "drugs," "bioactive agents" "pharmaceuticals," "pharmaceutically active agents" and other related terms may be used interchangeably herein. Therapeutic agents may be used singly or in combination.

In certain embodiments, the slings of the present disclosure may comprise one or more therapeutic agents, for example, selected from the following, among many others: (a) female hormones such as estrogen (including estrogen cocktails) and progesterone, (b) anti-inflammatory agents including corticosteroids such as hydrocortisone and prednisolone, and non-steroidal anti-inflammatory drugs (NSAIDS) such as aspirin, ibuprofen, and naproxen; (c) narcotic and non-narcotic analgesics and local anesthetic agents (e.g., for purposes of minimizing pain); (d) growth factors such as epidermal growth factor and transforming growth factor-α (e.g., for purposes of stimulate the healing process and or promoting growth of collagenous tissue); (e) antimicrobial agents including chlorhexidine, triclosan, nitrofurazone, benzalkonium chlorides, silver salts, silver particles, metallic silver and antibiotic agents such as the penicillins (e.g., penicillin G, methicillin, oxacillin, ampicillin, amoxicillin, ticarcillin, etc.), the cephalosporins (e.g., cephalothin, cefazolin, cefoxitin, cefotaxime, cefaclor, cefoperazone, cefixime, ceftriaxone, cefuroxime, etc.), the carbapenems (e.g., imipenem, metropenem, etc.), the monobactems (e.g., aztreonem, etc.), the carbacephems (e.g., loracarbef, etc.), the glycopeptides (e.g., vancomycin, teichoplanin, etc.), bacitracin, polymyxins, colistins, fluoroquinolones (e.g., norfloxacin, lomefloxacin, fleroxacin, ciprofloxacin, enoxacin, trovafloxacin, gatifloxacin, etc.), sulfonamides (e.g., sulfamethoxazole, sulfanilamide, etc.), diaminopyrimidines (e.g., trimethoprim, etc.), rifampin, aminoglycosides (e.g., streptomycin, neomycin, netilmicin, tobramycin, gentamicin, amikacin, etc.), tetracyclines (e.g., tetracycline, doxycycline, demeclocycline, minocycline, etc.), spectinomycin, macrolides (e.g., erythromycin, azithromycin, clarithromycin, dirithromycin, troleandomycin, etc.), and oxazolidinones (e.g., linezolid, etc.), (f) anti-collagenase agents (collagenase inhibitors) including tetracycline compounds such as doxycycline, bacitracin, prednisolone, medroxyprogesterone, cysteine, acetylcysteine, N-acetylcysteine, sodium citrate, edetic acid (EDTA), TIMP-1 and TIMP-2, (g) anti-elastase agents (elastase inhibitors) such as alpha-1-protease inhibitor, alpha-1-antitrypsin, secretory leukocyte protease inhibitor, glycosaminoglycans (e.g., heparin), elastase inhibitor I, elastase inhibitor II, elastase inhibitor III, elastase inhibitor IV, peptide aldehydes, caffeic acid, elafin, ceramides, nicardipine, procyanidins, proanthocyanidins, coumarinic derivatives, sivelestat (e.g., sivelestat sodium salt), 6-amino-2-phenyl-4H-3,1-benzoxazin-4-one aminoacyl, and dipeptidyl derivatives, (h) pharmaceutically acceptable salts, esters and other derivatives of the foregoing, and (i) combinations of two or more of the foregoing.

Additional agents for use in conjunction with the slings of the present disclosure also include imaging agents including (a) contrast agents for use in connection with x-ray fluoroscopy, including metals, metal salts and oxides (particularly bismuth salts and oxides), and iodinated compounds, among others, (b) contrast agents for use in conjunction with ultrasound imaging, including organic and inorganic echogenic particles (i.e., particles that result in an increase in the reflected ultrasonic energy) or organic and inorganic echolucent particles (i.e., particles that result in a decrease in the reflected ultrasonic energy), and (c) contrast agents for use in conjunction with magnetic resonance imaging (MRI), including contrast agents that contain elements with relatively large magnetic moment such as Gd(III), Mn(II), Fe(III) and compounds (including chelates) containing the same, such as gadolinium ion chelated with diethylenetriaminepentaacetic acid.

In various embodiments, the slings may contain from less than 1 wt % to 50 wt % or more of one or more of the preceding additional agents.

In another aspect of the disclosure, medical kits useful in sling procedures are provided. The medical kits may include all or a subset of all the components useful for performing the procedures. For example, the medical kits may comprise any combination of any two, three, four, or more of the following items: (a) a surgical sling, either without or with an associated bonding material, (b) a bonding material, for example, in fluid form or solid form, (c) a surgical instrument (e.g., one that can hold and place a surgical sling), (d) an energy source (e.g., in a stand-along unit or associated with a surgical instrument), (e) suitable packaging material, and (f) printed material with one or more of the following: (i) storage information and (ii) instructions regarding how to implant the surgical sling in a subject.

Although various embodiments are specifically illustrated and described herein, it will be appreciated that modifications and variations of the present disclosure are covered by the above teachings and are within the purview of the appended claims without departing from the spirit and intended scope of the invention.

What is claimed is:

1. A method of attaching a surgical sling, the method comprising:

inserting an end portion of sling material into an incision or puncture in patient tissue using a delivery instrument having a deployment mechanism, an energy source, and an energy emitting tip, the end portion of the sling material including bonding material, the end portion of the sling being coupled to the energy emitting tip; and activating the deployment mechanism causing the end portion of the sling material to be pushed off the energy emitting tip while simultaneously activating the energy source to apply energy to the bonding material via the energy emitting tip such that the bonding material is activated and the end portion of the sling material is attached to the patient tissue.

2. The method of claim 1, wherein the energy source includes a light energy source, a microwave energy source, a radio frequency energy source, an infrared energy source, a radiation source, or a plasma energy source.

3. The method of claim 1, wherein the end portion of the sling material includes a carrier having a hollow cylindrical shape.

4. The method of claim 1, wherein the incision or puncture is formed in an obturator internus muscle or in an abdominal wall.

5. A surgical instrument comprising:
- a handle;
- an elongated member having a distal tip portion that is configured to couple and place a surgical sling in a subject;
- an energy source having an energy emitting tip disposed on the distal tip portion of the elongate member; and
- a deployment mechanism configured to push the surgical sling off the distal tip portion of the surgical instrument, wherein activation of the deployment mechanism also energizes the energy source to allow energy to be applied to an end portion of the surgical sling via the energy emitting tip.

6. The surgical instrument of claim 5, wherein the elongated member includes a curved portion.

7. The surgical instrument of claim 5, wherein the elongated member is dimensioned to implant the surgical sling in a human subject in a retropubic sling procedure, a transobturator sling procedure or a mini-sling procedure.

* * * * *